United States Patent
Mitsumata et al.

(10) Patent No.: US 11,890,338 B2
(45) Date of Patent: Feb. 6, 2024

(54) INACTIVATED WHOLE-VIRUS INFLUENZA VACCINE AND METHOD FOR PREPARING SAME

(71) Applicants: DENKA COMPANY LIMITED, Chuo-ku (JP); NATIONAL UNIVERSITY CORPORATION KUMAMOTO UNIVERSITY, Kumamoto (JP)

(72) Inventors: Ryotaro Mitsumata, Gosen (JP); Shogo Misumi, Kumamoto (JP); Naoki Kishimoto, Kumamoto (JP); Takuma Gotanda, Gosen (JP); Nagisa Nakata, Gosen (JP)

(73) Assignees: DENKA COMPANY LIMITED, Chuo-ku (JP); NATIONAL UNIVERSITY CORPORATION KUMAMOTO UNIVERSITY, Kumamoto (JP)

( * ) Notice: Subject to any disclaimer, the term of this patent is extended or adjusted under 35 U.S.C. 154(b) by 0 days.

(21) Appl. No.: 17/279,898

(22) PCT Filed: Sep. 26, 2019

(86) PCT No.: PCT/JP2019/037884
§ 371 (c)(1),
(2) Date: Mar. 25, 2021

(87) PCT Pub. No.: WO2020/067301
PCT Pub. Date: Apr. 2, 2020

(65) Prior Publication Data
US 2022/0031833 A1 Feb. 3, 2022

(30) Foreign Application Priority Data

Sep. 26, 2018 (JP) ................................ 2018-181039

(51) Int. Cl.
| | | |
|---|---|---|
| *A61K 39/145* | (2006.01) | |
| *A61P 31/16* | (2006.01) | |
| *C12N 15/113* | (2010.01) | |
| *A61K 39/00* | (2006.01) | |

(52) U.S. Cl.
CPC ............ *A61K 39/145* (2013.01); *A61P 31/16* (2018.01); *C12N 15/1131* (2013.01); *A61K 2039/5252* (2013.01)

(58) Field of Classification Search
None
See application file for complete search history.

(56) References Cited

U.S. PATENT DOCUMENTS

2017/0128363 A1* 5/2017 Kamishita ................ C12N 7/00
2017/0196965 A1   7/2017 Kimachi et al.

FOREIGN PATENT DOCUMENTS

| CN | 102068592 A | 5/2011 |
| WO | WO 2016/010081 A1 | 1/2016 |
| WO | WO 2016/207853 A2 | 12/2016 |

OTHER PUBLICATIONS

Pieler et al., A cell culture-derived whole virus influenza A vaccine based on magnetic sulfated cellulose particles confers protection in mice against lethal influenza A virus infection, Vaccine, 2016, vol. 34, pp. 6367-6374.*
International Search Report dated Dec. 10, 2019 in PCT/JP2019/037884, 2 pages.
Marine, W.M., et al., "Reactions and serologic responses in young children and infants after administration of inactivated monovalent influenza A vaccine", J. Pediatr., Jan. 1976; 88(1):26-30.
Wright, P.F. et al., "Clinical reactions and serologic response following inactivated monovalent influenza type B vaccine in young children and infants", The Journal of Pediatrics, Jan. 1976; 88(1): 31-35.
Gross P.A. et al., "A Controlled Double-Blind Comparison of Reactogenicity, Immunogenicity, and Protective Efficacy of Whole-Virus and Split-Product Influenza Vaccines in Children", J. Infect. Dis., Nov. 1977;136(5):623-32.
McElhaney J.E. et al., "Antibody response to whole-virus and split-virus influenza vaccines in successful ageing", Vaccine. 1993;11(10):1055-60.
Hardy CT et al., "Egg flu ids and cells of the chorioallantoic membrane of embryonated chicken eggs can select different variants of influ enza A (H3N2) viruses", Virology, 1995, vol. 211, pp. 302-336.
Kawana Akihiko, "Special issue, The latest information on influenza and its countermeasures -From One Health perspective—7. Current status and future of influenza vaccine", Medicine and Drug Journal, 2015, vol. 51, No. 10, pp. 2397-2400.
Chen I. et al., "The role of exosomes in semen in suppressing natural and vaccine-induced immunity", Topics in Antiviral Medicine, 2015, vol. 23, Issue e-1, pp. 151-152.
Extended European Search Report dated Jun. 10, 2022 in European Patent Application No. 19865376.6, 9 pages.
Haredy, A.M., et al., "An MDCK Cell Culture-Derived Formalin-Inactivated Influenza Virus Whole-Virion Vaccine from an Influenza Virus Library Confers Cross-Protective Immunity by Intranasal Administration in Mice", Clin Vaccine Immunol. Jul. 1, 2013. vol. 20, No. 7, XP055397238, pp. 998-1007.
Kistner, O., et al., "Cell culture (Vero) derived whole virus (H5N1) vaccine based on wild-type virus strain induces cross-protective immune responses", Vaccine, Jul. 20, 2007, vol. 25, No. 32, XP022162338. pp. 6028-6036.

* cited by examiner

*Primary Examiner* — Benjamin P Blumel
(74) *Attorney, Agent, or Firm* — Oblon, McClelland, Maier & Neustadt, L.L.P.

(57) ABSTRACT

An inactivated whole-virus influenza vaccine may have its antibody-inducing ability is maintained or enhanced and may cause fewer side reactions. A method for preparing an inactivated whole-virus influenza vaccine may use an embryonated chicken egg method, including subjecting a virus solution including a whole influenza virus collected from embryonated chicken eggs to a hypotonic treatment.

4 Claims, 4 Drawing Sheets

INACTIVATED WHOLE-VIRUS INFLUENZA VACCINE AND METHOD FOR PREPARING SAME

TECHNICAL FIELD

The present invention relates to an inactivated whole-virus influenza vaccine having a high antibody-inducing ability and reduced pyrogenicity, and a method for preparing the same.

BACKGROUND ART

Influenza virus belongs to the family of Orthomyxoviridae and is a virus classified as types A, B, C, and D depending on the difference in the antigenicity of the nucleoprotein and the matrix protein present in the virus. Type A and type B cause annual epidemics and in particular, children and elderly people may be severely affected due to viral infection. As prophylaxis against influenza virus infection, influenza vaccination is known and the influenza vaccine is a multivalent vaccine containing each antigen of two type A strains and one or two type B strains.

As the influenza vaccine, inactivated whole-virus vaccines obtained by inoculating a vaccine strain into incubated chicken eggs, followed by culturing, collecting, purifying and inactivating the virus with formaldehyde had been used in Japan until 1971. However, due to the problem of side reactions such as local reactions and fever (Non Patent Literature 1 and Non Patent Literature 2), split vaccines obtained by disrupting virus particles with an ether treatment and removing lipids in the envelope are distributed in the market since 1972. The split vaccine is a vaccine which has reduced local reactions and exothermic reactions and are excellent in safety, but has a problem of low antibody induction in children who have a little previous history of influenza virus and a little vaccination history and elderly people who have a declined immune function.

In contrast, since the inactivated whole-virus vaccine includes virus genomes which activate innate immunity, it has a high antibody-inducing ability even in children and elderly people as compared with the split vaccine (Non Patent Literature 3 and Non Patent Literature 4). Therefore, its improvement has been examined in recent years. For example, Patent Literature 1 discloses that virus-like particles obtained by fixing virus particles with, for example, aldehydes and then subjecting them to a delipidation treatment exhibit higher immunogenicity (antibody induction), as compared with the split vaccine and can reduce the exothermic reactions.

CITATION LIST

Patent Literature

Patent Literature 1: WO 2016/010081

Non Patent Literature

Non Patent Literature 1: Marine, W. M., et al., Reactions and serologic response in young children and infants after administration of inactivated monovalent influenza A vaccine. J. Pediatr. 1976 January; 88(1):26-30

Non Patent Literature 2: Wright, P. F., et al., Clinical reactions and serologic response following inactivated monovalent influenza type B vaccine in young children and infants. J. Pediatr. 1976 January; 88(1):31-35

Non Patent Literature 3: Gross P. A., Ennis F. A., Gaerlan P. F., Denson L. J., Denning C. R., Schiffman D., A controlled double-blind comparison of reactogenicity, immunogenicity, and protective efficacy of whole-virus and split-product influenza vaccines in children. J Infect Dis. 1977 November; 136(5):623-32.

Non Patent Literature 4: McElhaney J. E., Meneilly G. S., Lechelt K. E., Beattie B. L., Bleackley R. C., Antibody response to whole-virus and split-virus influenza vaccines in successful ageing. Vaccine. 1993; 11(10):1055-60.

SUMMARY OF INVENTION

Technical Problem

The present invention relates to a provision of an inactivated whole-virus influenza vaccine which has a maintained or enhanced antibody-inducing ability and causes less side reactions.

Solution to Problem

The inventors of the present application have conducted intensive studies and, as a result, have found that an inactivated whole-virus vaccine prepared by concentrating and purifying an influenza virus suspension propagated in embryonated chicken eggs contains extracellular vesicle components derived from the embryonated chicken eggs. Surprisingly, the inventors have also found that an inactivated whole-virus vaccine having a reduced content of extracellular vesicles can be obtained by exposing the virus solution to a hypotonic solution during the preparation process of the whole-virus vaccine, and this vaccine has a high antibody-inducing ability and a reduced pyrogenic activity.

That is, the present invention relates to the following 1) to 6).

1) A method for preparing an inactivated whole-virus influenza vaccine using an embryonated chicken egg method, comprising a step of subjecting a virus solution comprising whole influenza virus particles collected from embryonated chicken eggs to a hypotonic treatment.

2) The method according to 1), wherein the hypotonic treatment is exposing the virus solution to a hypotonic solution.

3) The method according to 2), wherein the hypotonic solution is an aqueous solution of 160 mOsm/kg or less, and preferably 110 mOsm/kg or less.

4) The method according to any one of 1) to 3), wherein the hypotonic treatment is subjected on the virus solution which has been inactivated.

5) An inactivated whole-virus influenza vaccine prepared using the method according to any one of 1) to 4).

6) An inactivated whole-virus influenza vaccine prepared using an embryonated chicken egg method, wherein the vaccine has a reduced content of extracellular vesicle components derived from embryonated chicken eggs.

Advantageous Effects of Invention

According to the present invention, an inactivated whole-virus influenza vaccine having a high antibody-inducing ability and reduced pyrogenicity can be provided.

DESCRIPTION OF EMBODIMENTS

In the present invention, the "influenza vaccine" means a vaccine containing at least one antigen of either influenza A virus or influenza B virus. That is, the influenza vaccine of the present invention may be a monovalent vaccine containing only one of influenza A virus or influenza B virus, or may be a multivalent vaccine containing both of them.

In the present invention, the "influenza virus" refers to the influenza A virus or the influenza B virus, or both of them. The influenza virus also includes all currently known subtypes and subtypes which will be isolated and identified in the future.

The influenza virus strain used for the vaccine preparation of the present invention may be a strain isolated from infected animals or patients, or may be a recombinant virus established in cultured cells in a genetic engineering manner.

In the present invention, the "whole influenza virus particles" mean virus particles that can be obtained by culturing an influenza virus and retain the form of the virus, and the "inactivated whole-virus influenza vaccine" refers to a vaccine containing the virus particles which has been inactivated.

The method for preparing the inactivated whole-virus influenza vaccine of the present invention is a preparation method using an embryonated chicken egg method and comprises a hypotonic treatment step.

The "embryonated chicken egg method" refers to a method in which a virus strain is inoculated into incubated chicken eggs and cultured, and then the virus suspension is clarified, concentrated, purified, and inactivated to obtain a virus solution containing virus particles.

As used herein, culturing is performed by inoculating an influenza virus strain into incubated chicken eggs and culturing the strain at from 30 to 37° C. for about from 1 to 7 days, and preferably at from 33 to 35° C. for about 2 days. After termination of culturing, the virus suspension (infected allantoic fluid) is collected, and centrifuged or filtered for clarification. Then, ultrafiltration is performed for concentration. The virus purification can be performed using a means including ultracentrifugation such as sucrose density gradient centrifugation or liquid chromatography.

The purified virus solution is subjected to an inactivation treatment. Examples of the method for inactivating viruses include a formalin treatment, and a treatment with, for example, ultraviolet irradiation, beta propiolactone, and binary ethylenimine.

In the present invention, a hypotonic treatment is performed at any timing until clarifying, concentrating, purifying, and inactivating the influenza virus suspension cultured in and collected from embryonated chicken eggs to obtain a vaccine.

Examples of the "hypotonic treatment" include exposure of the virus solution containing the whole influenza virus particles collected from embryonated chicken eggs after culturing to a hypotonic solution. Thereby it is considered that the influenza virus having a scaffold protein (Ml protein) in the envelope can retain its particle shape, whereas the particles of extracellular vesicles (such as exosomes, microvesicles, or apoptotic vesicles) derived from embryonated chicken eggs having no scaffold protein swell and rupture.

Examples of the hypotonic solution used herein include an aqueous solution of 160 mOsm/kg or less, preferably 110 mOsm/kg or less, and more preferably 32 mOsm/kg or less. The aqueous solution can contain an additive such as a buffer, a dispersing agent, and a pH adjuster.

Preferred examples of the hypotonic solution include a 10 mM Tris-HCl buffer solution, a 10 mM Tris-HCl buffer solution containing 0.5 w/w % sucrose, a 10 mM Tris-HCl buffer solution containing 0.2 w/w % sucrose and 1 mM ethylenediamine tetraacetic acid.

Examples of means for the exposure of the virus solution to the hypotonic solution is not particularly limited, but include replacing the buffer with the hypotonic solution in dialysis or ultrafiltration, or suspending the virus solution precipitated by centrifugation in the hypotonic solution.

The hypotonic treatment can be performed before or after the clarification step, before or after the concentration step, before or after the purification step, or before or after the inactivation step. It is preferably performed before or after the inactivation step, and more preferably after the inactivation step.

In the inactivated whole-virus influenza vaccine of the present invention thus prepared, extracellular vesicle components derived from contaminated embryonated chicken eggs are reduced (Examples 1 and 2).

As used herein, "extracellular vesicle components are reduced" means that when the vaccine prepared by the method of the present invention is compared with a vaccine prepared in the same manner except for not subjecting to a hypotonic treatment, the content of extracellular vesicle components contained therein is reduced, and reduced by preferably 30% or more, more preferably 50% or more, even more preferably 80% or more, and even more preferably 90% or more. Alternatively, it means that, when the vaccine prepared by the method of the present invention is observed with a transmission electron microscope, the presence ratio of the extracellular vesicles with respect to the virus particles is preferably 55% or less, more preferably 35% or less, even more preferably 25% or less, and even more preferably 20% or less.

In addition, the antibody-inducing ability of the inactivated whole-virus influenza vaccine of the present invention is high as compared with that of the split vaccine, and is equal to or higher as compared with that of an inactivated whole-virus influenza vaccine not exposed to a hypotonic solution. Also, the pyrogenicity is reduced as compared with that of the inactivated whole-virus influenza vaccine not exposed to a hypotonic solution (Examples 3 to 6).

The inactivated whole-virus influenza vaccine of the present invention preferably has a concentration of whole influenza virus particles of 2,000 μg HA/mL or less, and more preferably 1,200 μg HA/mL or less. The concentration can be measured by a single radial immunodiffusion test shown in Reference Example 2 described below. In the inactivated whole-virus influenza vaccine of the present invention, the amount of the antigen contained in the vaccine may be appropriately changed depending on the kind of virus or the subject to be administered.

The inactivated whole-virus influenza vaccine of the present invention may further contain a pharmaceutically acceptable carrier, in addition to the whole influenza virus particles. Examples of the carrier include a carrier usually used for producing vaccines, and specific examples thereof include a buffer, an emulsifying agent, a preservative (e.g., thimerosal), an isotonizing agent, a pH adjuster, an inactivation agent (e.g., formalin or beta propiolactone), and an adjuvant (e.g., aluminum hydroxide gel).

The dosage form of the inactivated whole-virus influenza vaccine of the present invention may be, for example, a liquid, a lyophilized powder, a capsule, or a tablet.

The route of administration of the inactivated whole-virus influenza vaccine of the present invention may be, for example, subcutaneous administration, intramuscular administration, intradermal administration, nasal administration, sublingual administration, or oral administration, and the administration method thereof may be, for example, administration methods by using syringe, microneedle, syringe equipped with a microneedle, transdermal patch, or spray.

EXAMPLES

Hereinafter, the present invention will be described in detail by way of Examples, but the present invention is not limited thereto, in any way.

Reference Example 1 Isolation of Extracellular Vesicles Contained in Chorioallantoic Fluid of Uninfected Eggs Seventy-two, 11 day-old embryonated chicken eggs were cooled at 4° C. for 1 hour or more, and the chorioallantoic fluid was collected from each embryonated chicken egg using a disposable injection needle and syringe (manufactured by TERUMO CORPORATION). The collected chorioallantoic fluid was pooled, and centrifuged at 4° C., 300×g for 10 minutes, and the obtained supernatant was further centrifuged by using an ultracentrifuge (manufactured by Hitachi Koki Co., Ltd.) at 4° C., 141,000×g for 4 hours. The precipitate after ultracentrifugation was suspended in 6.7 mM phosphate buffered saline (pH 7.2), and centrifuged again at 4° C., 141,000×g for 4 hours. The obtained precipitate was suspended in 6.7 mM phosphate buffered saline (pH 7.2) to obtain an extracellular vesicle suspension.

On a grid for a TEM electron microscope with a collodion support film (manufactured by Okenshoji Co., Ltd.), 5 μL of 0.1% poly-L-lysine solution was added dropwise and allowed to stand at room temperature for 1 minute. After standing, the excess poly-L-lysine solution was absorbed with a filter paper, 5 μL of the extracellular vesicle suspension prepared as described above was added dropwise thereto and then allowed to stand at room temperature for 5 minutes. Thereafter, the excess extracellular vesicle suspension was absorbed with a filter paper, and 5 μL of 2% phosphotungstic acid stain was added dropwise thereto to stain negatively. The stained sample was observed and photographed with a transmission electron microscope (manufactured by JEOL Ltd.).

Figure 1:
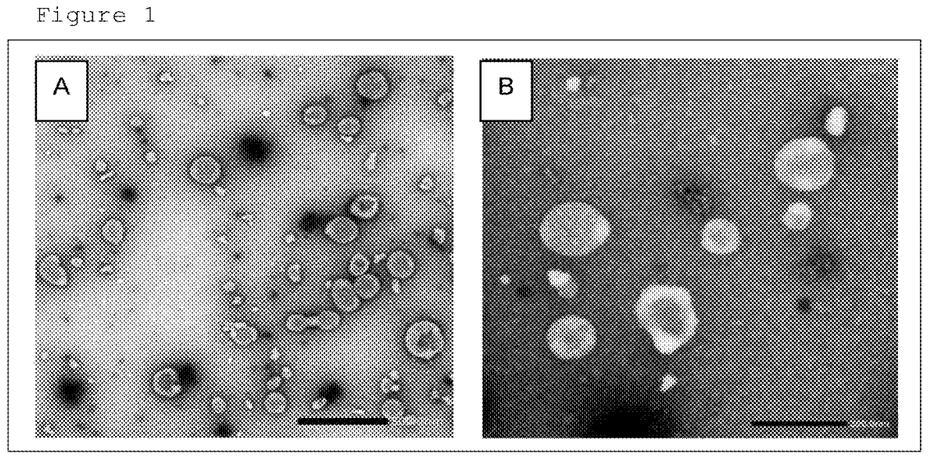
FIGS. 1A and 1B are electron micrographs of extracellular vesicle components obtained by collecting, purifying, and concentrating the chorioallantoic fluid of uninfected embryonated chicken eggs. A: Extracellular vesicles derived from the chorioallantoic fluid of embryonated chicken eggs (15,000 times), B: extracellular vesicles derived from the chorioallantoic fluid of embryonated chicken eggs (40,000 times).

It was thus confirmed that vesicles having various particle sizes were present in the chorioallantoic fluid of embryonated chicken eggs even in the virus uninfected state, as shown in FIG. 1. Since these extracellular vesicles probably have a lower density of protein than virus particles, the stain was flowed into the vesicles and these vesicles were observed as grey particles.

Example 1 Preparation and Hypotonic Treatment of Inactivated Whole-Virus Vaccine of B/Victoria Lineage A B/Texas/2/2013 strain was inoculated into the chorioallantoic cavity of 12 day-old embryonated chicken eggs and cultured for 2 days, and then the chorioallantoic fluid was collected. The collected chorioallantoic fluid was clarified by filter filtration, then adsorbed on barium sulfate salt, and eluted with 12% sodium citrate solution to collect the influenza virus. The solution of the collected virus was further replaced with 6.7 mM phosphate buffered saline (pH 7.2) by ultrafiltration. After replacement of buffer, a fraction containing the influenza virus was collected by sucrose density gradient centrifugation to thereby complete purification. To this purified influenza virus, beta propiolactone as an inactivation agent was added to have a final concentration of 0.05%, followed by allowing the mixture to react at 4° C. for 24 hours to inactivate the infectivity of the influenza virus. After this inactivation reaction, the buffer was replaced with 6.7 mM phosphate buffered saline containing 1 w/w % sucrose (pH 7.2) by ultrafiltration (MWCO: 100,000), which was used as an inactivated whole-virus vaccine (B15VT-19-S151028).

The inactivated whole-virus vaccine (B15VT-19-S151028) prepared as described above was replaced with 10 mM Tris-HCl buffer solution (pH 7.2, 17 mOsm/kg) by ultrafiltration (MWCO: 100,000), and after the replacement, it was allowed to stand at 4° C. overnight (hypotonic treatment). After the hypotonic treatment, the buffer was replaced with 6.7 mM phosphate buffered saline containing 1 w/w % sucrose (pH 7.2) by ultrafiltration (MWCO: 100,000), which was used as an inactivated whole-virus vaccine subjected to a hypotonic treatment (BV170729-10T).

Figure 2:
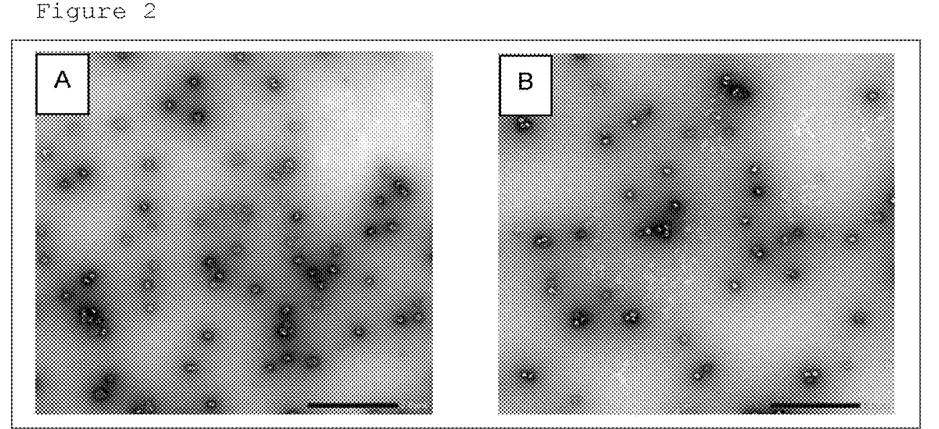
FIGS. 2A and 2B are electron micrographs of the inactivated whole-virus vaccine of the B/Victoria lineage (B15VT-19-S151028) and the inactivated whole-virus vaccine subjected to a hypotonic treatment (BV170729-10T). A: Inactivated whole-virus vaccine (4,000 times), B: inactivated whole-virus vaccine subjected to a hypotonic treatment (4,000 times).

The inactivated whole-virus vaccine and the inactivated whole-virus vaccine subjected to a hypotonic treatment were observed and photographed with a transmission electron microscope (manufactured by JEOL Ltd.) by the above-described method. As a result, the number of virus particles observed as white particles and the number of extracellular vesicles observed as grey particles were about equal in the inactivated whole-virus vaccine (FIG. 2A). On the other hand, it was found in the inactivated whole-virus vaccine subjected to a hypotonic treatment that the ratio of the number of extracellular vesicles as grey particles with respect to the number of virus particles as white particles was reduced (although in the whole-virus particles 82% extracellular vesicles were present with respect to the virus, the presence ratio of extracellular vesicles was reduced to 51% by the hypotonic treatment) (FIG. 2B).

Example 2 Preparation and Hypotonic Treatment of Inactivated Whole-Virus Vaccine of B/Yamagata Lineage A B/Phuket/3073/2013 strain was inoculated into the chorioallantoic cavity of 12 day-old embryonated chicken eggs and cultured for 2 days, and the chorioallantoic fluid was collected. The collected chorioallantoic fluid was clarified by filter filtration, adsorbed on barium sulfate salt, eluted with 12% sodium citrate solution to collect the influenza virus. The solution of the collected virus was further replaced with 6.7 mM phosphate buffered saline (pH 7.2) by ultrafiltration. After replacement of buffer, a fraction containing the influenza virus was collected by sucrose density gradient centrifugation to thereby complete purification. To this purified influenza virus, beta propiolactone as an inactivation agent was added to have a final concentration of 0.05°, followed by allowing the mixture to react at 4° C. for 24 hours to inactivate the infectivity of the influenza virus. After the inactivation reaction, the buffer was replaced with 6.7 mM phosphate buffered saline containing 1 w/w % sucrose (pH 7.2) by ultrafiltration (MWCO: 100,000), which was used as an inactivated whole-virus vaccine (BYBPL170905).

The inactivated whole-virus vaccine (BYBPL170905) prepared as described above was replaced with 10 mM Tris-HCl buffer solution containing 0.5 w/w % sucrose (pH 7.2, 32 mOsm/kg) by ultrafiltration (MWCO: 100,000), and after the replacement, it was allowed to stand at 4° C. overnight (hypotonic treatment). After the hypotonic treatment, the buffer was replaced with 6.7 mM phosphate buffered saline containing 1 w/w° sucrose (pH 7.2) by ultrafiltration (MWCO: 300,000), which was used as an inactivated whole-virus vaccine subjected to a hypotonic treatment by ultrafiltration (HYPBY170913).

Also, an inactivated whole-virus vaccine of the B/Phuket/3073/2013 strain was prepared by the above-described method, an equivalent amount of 10 mM Tris-HCl buffer solution containing 0.2 w/w % sucrose and 1 mM ethylenediamine tetraacetic acid was added thereto, and the mixture was centrifuged at 4° C., 11,910×g for 4 hours to obtain a precipitate of the virus. To this precipitate of this virus, 10 mM Tris-HCl buffer solution containing 0.2 w/w % sucrose and 1 mM ethylenediamine tetraacetic acid (24 mOsm/kg) was added and suspended, and then it was allowed to stand at 10° C. or less for 15 hours (hypotonic treatment). After the hypotonic treatment, the suspension was centrifuged again at 4° C., 11,910×g for 4 hours to precipitate the virus, and the precipitate of the virus was suspended in 6.7 mM phosphate buffered saline containing 1 w/w % sucrose (pH 7.2). The buffer of this suspension was further replaced with 6.7 mM phosphate buffered saline containing 1 w/w % sucrose (pH 7.2) by ultrafiltration (MWCO: 300,000), which was used as an inactivated whole-virus vaccine subjected to a hypotonic treatment by centrifugation (17BY-OST171129).

Figure 3:
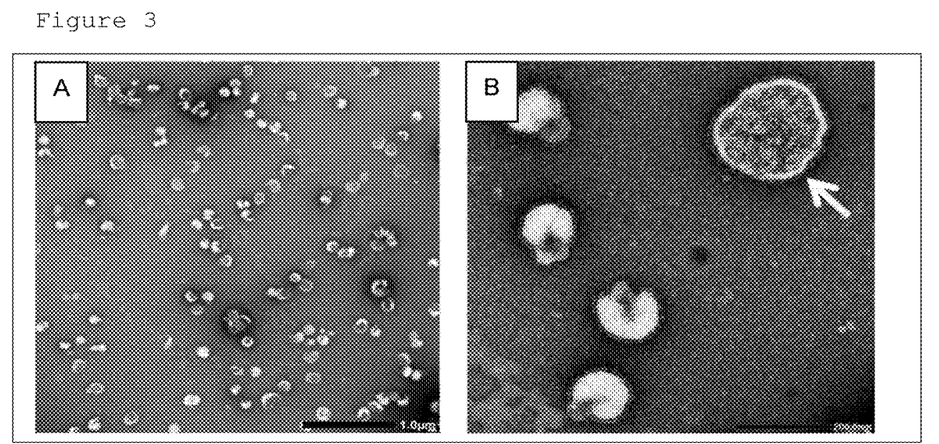
FIGS. 3A and 3B are electron micrographs of the inactivated whole-virus vaccine (BYBPL170905) of the B/Yamagata lineage. A: 8,000 times, B: 40,000 times.

The inactivated whole-virus vaccine (BYBPL170905) and two kinds of inactivated whole-virus vaccines subjected to a hypotonic treatment (HYPBY170913 and 17BY-OST171129) were observed and photographed with a transmission electron microscope (manufactured by JEOL Ltd.) by the above-described method. As a result, a lot of extracellular vesicles were observed in the observation of the inactivated whole-virus vaccine at low magnification (FIG. 3A). FIG. 3B is an image at high magnification and an extracellular vesicle is indicated by an arrow.

Figure 4:
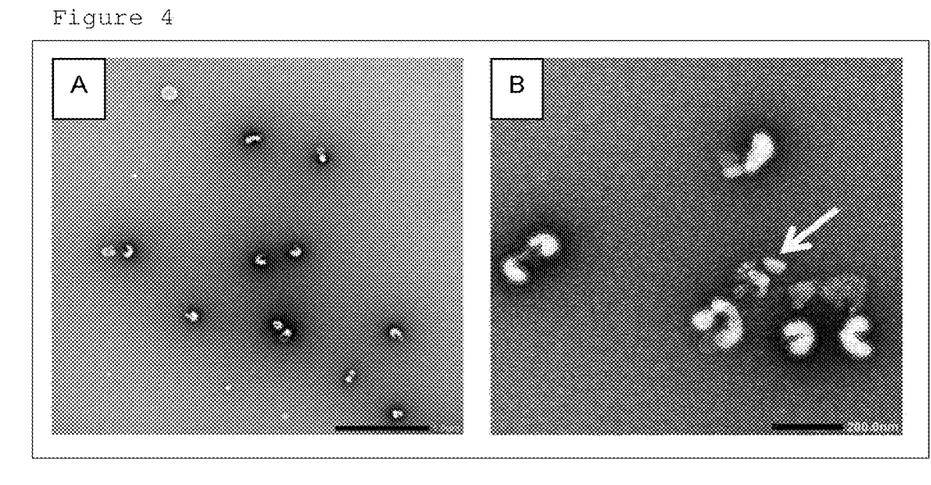
FIGS. 4A and 4B are electron micrographs of the inactivated whole-virus vaccine subjected to a hypotonic treatment by ultrafiltration (HYPBY170913) of the B/Yamagata lineage. A: 8,000 times, B: 30,000 times.
Figure 5:
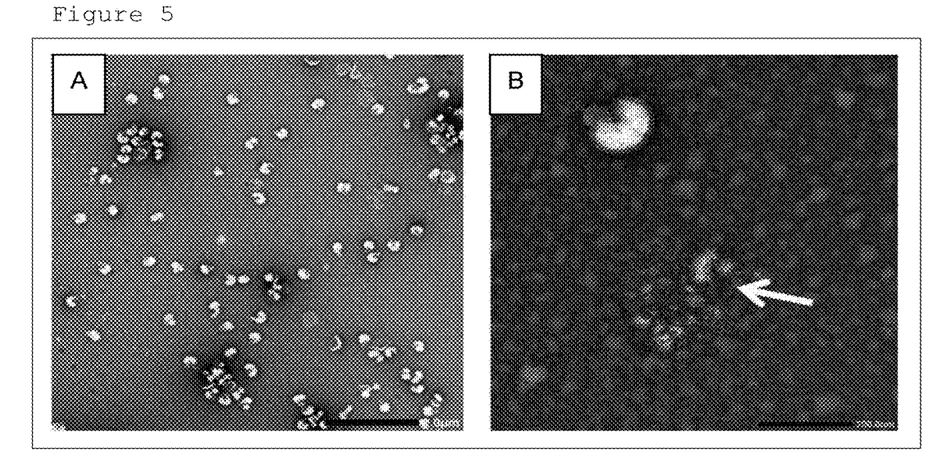
FIGS. 5A and 5B are electron micrographs of the inactivated whole-virus vaccine (17BY-OST171129) of the B/Yamagata lineage obtained by subjecting a precipitate after centrifugation to a hypotonic treatment. A: 8,000 times, B: 40,000 times.

FIG. 4 shows electron micrographs of the inactivated whole-virus vaccine subjected to a hypotonic treatment by ultrafiltration (HYPBY170913). It was observed in the image at low magnification (FIG. 4A) that extracellular vesicles were reduced as compared with those in the inactivated whole-virus vaccine (BYBPL170905) (in the whole-virus 108% extracellular vesicles were present with respect to the virus, whereas the presence ratio of extracellular vesicles was reduced to 23% by the hypotonic treatment), and in the image at high magnification (FIG. 4B) fragments of disrupted particles as indicated by an arrow were observed. Also in the inactivated whole-virus vaccine subjected to a hypotonic treatment by centrifugation (17BY-OST171129), it was observed in the image at low magnification (FIG. 5A) that extracellular vesicles were reduced as compared with those in the inactivated whole-virus vaccine (BYBPL170905) (although in the whole-virus 108% extracellular vesicles were present with respect to the virus, the presence ratio of extracellular vesicles was reduced to 16% by the hypotonic treatment), and in the image at high magnification (FIG. 5B) that fragments of disrupted extracellular vesicles as indicated by an arrow were observed, similar to the inactivated whole-virus vaccine subjected to a hypotonic treatment by ultrafiltration.

Example 3 Pyrogen Test

Each of the inactivated whole-virus vaccine (BYBPL170905), the inactivated whole-virus vaccine subjected to a hypotonic treatment (HYPBY170913), and an inactivated whole-virus vaccine subjected to a high concentration formalin treatment as a control was diluted with 6.7 mM phosphate buffered saline (pH 7.2) to have a protein concentration of 134 μg/mL, 1 mL/kg of which was administrated to a rabbit weighing 1.50 to 1.99 kg (Japanese white rabbit, male). For the administration, three rabbits were used per sample, and the change of the body temperature was observed for 180 minutes after administration when setting the body temperature of 15 minutes before administration to 0.

The preparation of the inactivated whole-virus vaccine subjected to a high concentration formalin treatment as the control was performed in the same manner as the preparation of the above-mentioned inactivated whole-virus vaccine (BYBPL170905), starting from the inoculation of the embryonated chicken eggs until the purification by sucrose density gradient centrifugation, and formalin was added to the obtained purified influenza virus to have a final concentration of 0.08%, followed by allowing the mixture to react at 25° C. for 1 week to inactivate the infectivity of the influenza virus. After the inactivation reaction, the buffer was replaced with 6.7 mM phosphate buffered saline containing 1 w/w % sucrose (pH 7.2) by ultrafiltration (MWCO: 100,000), which was used as the inactivated whole-virus vaccine subjected to a high concentration formalin treatment (BYFMA170908).

Figure 6:
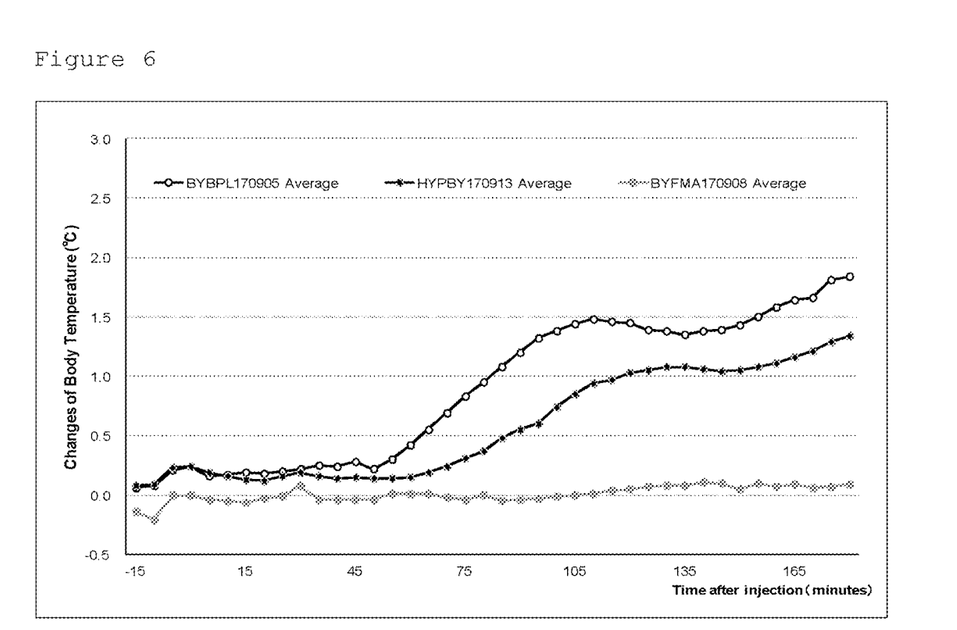
FIG. 6 shows the results of the rabbit pyrogen test of the inactivated whole-virus vaccine (BYBPL170905), the inactivated whole-virus vaccine subjected to a high concentration formaldehyde treatment (BYFMA170908), and the inactivated whole-virus vaccine subjected to a hypotonic treatment (HYPBY170913).

FIG. 6 shows the transition of the average value of the body temperature difference of the rabbits to which each sample was administered. No fever was caused by the inactivated whole-virus vaccine subjected to a high concentration formalin treatment, and exothermic reaction exceeding 1.5° C. was found in the inactivated whole-virus vaccine. On the other hand, the exothermic reaction was caused but reduced in the inactivated whole-virus vaccine subjected to a hypotonic treatment as compared with that in the inactivated whole-virus vaccine. A comparison between the body temperature difference after 180 minutes where the fever takes the maximum value shows that the exothermic reaction in the inactivated whole-virus vaccine subjected to a hypotonic treatment is lower by about 0.5° C. than that in the inactivated whole-virus vaccine.

Example 4 Immunogenicity Test (B/Yamagata Lineage)

The antibody-inducing ability of the inactivated whole-virus vaccine (BYBPL170905), the inactivated whole-virus vaccine subjected to a hypotonic treatment (HYPBY170913), and the inactivated whole-virus vaccine subjected to a high concentration formalin treatment (BYFMA170908) was evaluated by using mice. Each vaccine was administered subcutaneously to BALE/c mice (female, 5 week-old) at a dose of 7.5 µg as an amount of protein (5 mice per group). Three weeks after the administration, the mice were euthanized and whole blood was collected. After the blood collection, the blood serum was obtained by centrifugation, and IgG titers specific to the B/Phuket/3073/2013 strain were measured by ELISA using this blood serum.

Figure 7:
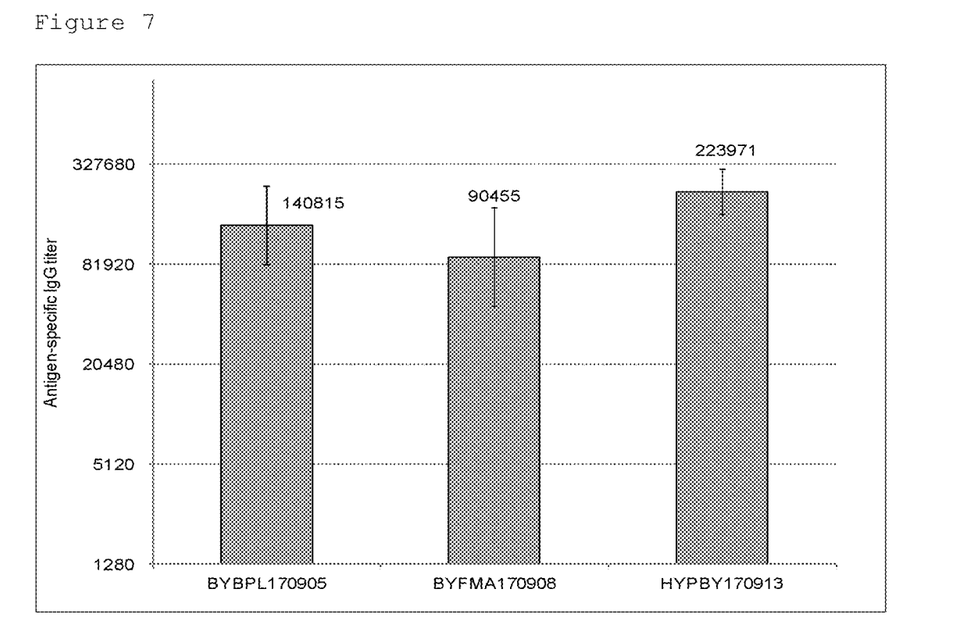
FIG. 7 shows the results of the immunogenicity test of the inactivated whole-virus vaccine (BYBPL170905), the inactivated whole-virus vaccine subjected to a high concentration formaldehyde treatment (BYFMA170908), and the inactivated whole-virus vaccine subjected to a hypotonic treatment (HYPBY170913).

FIG. 7 shows the results of the IgG titer measurement. A comparison between the geometric mean titers (hereinafter, GMT) shown in the figure shows that the inactivated whole-virus vaccine subjected to a hypotonic treatment-administered group had the highest titer, the inactivated whole-virus vaccine-administered group had the next highest titer, and the inactivated whole-virus vaccine subjected to a high concentration formalin treatment-administrated group had the lowest titer value. Therefore, it was indicated that, when the inactivated whole-virus vaccine is subjected to a high concentration formalin treatment, the antibody-inducing ability is reduced, whereas the antibody-inducing ability is increased in the inactivated whole-virus vaccine subjected to a hypotonic treatment.

Example 5 Immunogenicity Test (A/H3N2 Subtype)

An inactivated whole-virus vaccine (H3BPL170630), an inactivated whole-virus vaccine subjected to a hypotonic treatment by ultrafiltration (HYPH3170913), and an inactivated whole-virus vaccine subjected to a high concentration formalin treatment (H3FMA170713) of the A/Hong Kong/4801/2014 strain (A/H3N2 subtype) were prepared in accordance with the method of Examples 2 and 3. The antibody-producing ability of these vaccines in mice was evaluated in accordance with the method described in Example 4. In the present Example, the stock solution of the A/Hong Kong/4801/2014 strain of an influenza HA vaccine "SEIKEN" was used as a control, and this was used as a Split virion.

Figure 8:
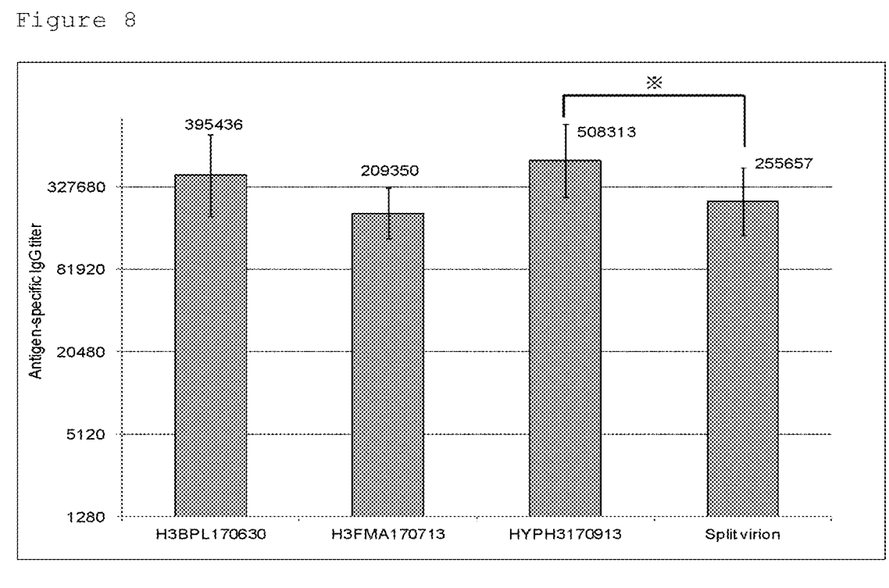
FIG. 8 shows the results of the immunogenicity test of the inactivated whole-virus vaccine (H3BPL170630), the inactivated whole-virus vaccine subjected to a high concentration formaldehyde treatment (H3FMA170713), the inactivated whole-virus vaccine subjected to a hypotonic treatment (HYPH3170913), and the split vaccine.

FIG. 8 shows the results of the IgG titer measurement. A comparison between the GMTs shown in the figure shows that the GMT was high in the order of the inactivated whole-virus vaccine subjected to a hypotonic treatment, the inactivated whole-virus vaccine, the Split virion, and the inactivated whole-virus vaccine subjected to a high concentration formalin treatment, and only the inactivated whole-virus vaccine subjected to a hypotonic treatment-administered group showed significantly higher antibody induction, as compared with the Split virion-administered group (Mann-Whitney U test, $p<0.05$). Therefore, similar to the results of the immunogenicity test for the B/Yamagata lineage, it was indicated that the hypotonic treatment improves the antibody-producing ability of the inactivated whole-virus vaccine.

The inactivated whole-virus vaccine subjected to a high concentration formalin treatment resulted in a lower antibody induction than the Split virion. While the high concentration formalin treatment caused no exothermic reaction in the pyrogen test of Example 3 and was excellent in safety, it had a lower antibody producing-ability than the commercially available Split virion, and is thus considered that the improvement of the efficacy is not expected.

Example 6 Evaluation of Cytokine-Producing Ability

The spleen was harvested from BALB/c mice (female, 11 week-old) and collected in a petri dish filled with HBSS (Thermo Scientific). The spleen was minced in HBSS, and after mincing, it was transferred to a conical tube. After allowing it to stand for about 3 minutes, the intermediate layer was collected while avoiding the precipitate and the floating materials, and the collected intermediate layer was centrifuged at room temperature, 200×g for 10 minutes. After centrifugation, the supernatant was discarded, a hemolysis buffer (17 mM Tris-HCl buffer solution containing 140 mM ammonium chloride) was added to the precipitate to break the red blood cells, and the mixture was centrifuged at 200×g for 10 minutes. The precipitate after centrifugation was washed with HBSS, and then, the precipitated spleen cells were suspended with RPMI-1640 containing 10% FBS, and the suspension was used as mouse spleen cells. To $1.0 \times 10^6$ mouse spleen cells, the inactivated whole-virus vaccine (BYBPL170905), the inactivated whole-virus vaccine subjected to a hypotonic treatment (HYPBY170913), and the inactivated whole-virus vaccine subjected to a high concentration formalin treatment (BYFMA170908) of the B/Yamagata lineage were added in an amount of 1 µg as an amount of protein and cultured under the conditions of 37° C. and 5% $CO_2$ for 24 hours. After culturing, the culture was centrifuged at room temperature, 600×g for 5 minutes, and the concentration of the cytokine produced in the culture supernatant by spleen cells was measured by Mouse Th1/Th2 essential 6 plex kit (eBioscience) and Bio-Plex (manufactured by Bio-Rad).

Table 1 shows the cytokine concentration of the culture supernatant. Although no IL-4 was produced by the stimulation of any vaccine, every other cytokines were most largely produced by the stimulation of the inactivated whole-virus vaccine subjected to a hypotonic treatment, followed by the inactivated whole-virus vaccine. The inactivated whole-virus vaccine subjected to a high concentration formalin treatment had the lowest production amount. The results are correlative to the results of the immunogenicity test of Example 4, and it is considered that the cytokine production from immune cells facilitated by the inactivated whole-virus vaccine is enhanced by the hypotonic treatment, and as a result, the antibody-inducing ability is also increased. On the other hand, it is considered that the cytokine production from immune cells is reduced by the high concentration formalin treatment, and as a result, the antibody-inducing ability is also reduced.

concentration of each sample to the standard antigen was calculated by parallel line assay.

The following Table 2 (B/Yamagata lineage) and Table 3 (A/H3N2 subtype) show the hemagglutinin concentration of each sample, the protein concentration, and the hemagglutinin content ratio to total protein. It should be noted that three kinds of inactivated whole-virus vaccines were prepared for each virus, but the same virus was used for the

TABLE 1

| Lot No. | IFN-γ pg/mL | SE | IL-12p70 pg/mL | SE | IL-4 pg/mL | SE | IL-5 pg/mL | SE | IL-6 pg/mL | SE | TNF-α pg/mL | SE |
|---|---|---|---|---|---|---|---|---|---|---|---|---|
| BYBPL170905 | 209.51 | 9.0 | 6.24 | 5.5 | ND | — | 5.49 | 12.2 | 101.07 | 20.5 | 85.66 | 22.0 |
| BYFMA170908 | 30.37 | 3.0 | ND | — | ND | — | ND | — | 51.46 | 5.5 | 45.91 | 13.5 |
| HYPBY170913 | 250.99 | 49.5 | 6.60 | 14.6 | ND | — | 7.12 | 18.3 | 120.73 | 11.0 | 105.45 | 18.5 |
| Media | 0.80 | 0 | ND | — | ND | — | ND | — | 2.83 | 5.0 | 6.44 | 10.0 |

Reference Example 2 Single Radial Immunodiffusion Test

Each hemagglutinin concentration of the inactivated whole-virus vaccine, the inactivated whole-virus vaccine subjected to a hypotonic treatment, and the inactivated whole-virus vaccine subjected to a high concentration formalin treatment of the B/Yamagata lineage and the A/H3N2 subtype was measured by the single radial immunodiffusion test. To each sample and a standard antigen, Zwittergent (trade name, manufactured by Merck Millipore) was added to have a final concentration of 1.0% and they were allowed to react for 30 minutes. After the reaction, each sample and the standard antigen to which Zwittergent was added were diluted with phosphate buffered saline containing 0.05 w/w % sodium azide (pH 7.4) to prepare a dilution series. This dilution series was added to each well of 1 w/v % agarose gel (hereinafter, SRD plate) into which a reference antiserum was added, and allowed to stand for 18 hours or more. After allowing to stand, the moisture of the SRD plate was absorbed with a filter paper, and each sample and the standard antigen were stained with Coomassie Brilliant Blue. After staining, the ring diameter of each sample and the standard antigen was measured and the hemagglutinin purified virus after the sucrose density gradient centrifugation which is a material for preparation.

When comparing the hemagglutinin content ratios, the inactivated whole-virus vaccine subjected to a hypotonic treatment was lower by about 5% than the inactivated whole-virus vaccine, and the inactivated whole-virus vaccine subjected to a high concentration formalin treatment was further lowered by 5%, in the B/Yamagata lineage. Also in the A/H3N2 subtype, the inactivated whole-virus vaccine and the inactivated whole-virus vaccine subjected to a hypotonic treatment had equivalent hemagglutinin content ratios, but the inactivated whole-virus vaccine subjected to a high concentration formalin treatment had a value lower by about 16 to 17% than them. Therefore, while the hemagglutinin concentration of the inactivated whole-virus vaccine was not largely varied by the hypotonic treatment, a 10% or more reduction was confirmed in the high concentration formalin treatment. This is considered due to cross-linking between proteins caused by an excess formalin treatment, and a low value of the hemagglutinin content ratio leads to a reduction in productivity and an increase in the total protein of a formulation, thereby increasing a concern for side reactions.

TABLE 2

| B/Yamagata lineage | Inactivated whole-virus vaccine | Inactivated whole-virus vaccine subjected to hypotonic treatment | Inactivated whole-virus vaccine subjected to high concentration formalin treatment |
|---|---|---|---|
| Lot No. | HYPBY170913 | BYBPL170905 | BYFMA170908 |
| Hemagglutinin concentration (μgHA/mL) | 1595 | 923 | 847 |
| Protein content (μg/mL) | 3837 | 2547 | 2700 |
| Hemagglutinin content ratio (%) | 41.57 | 36.24 | 31.37 |

TABLE 3

| A/H3N2 subtype | Inactivated whole-virus vaccine | Inactivated whole-virus vaccine subjected to hypotonic treatment | Inactivated whole-virus vaccine subjected to high concentration formalin treatment |
|---|---|---|---|
| Lot No. | H3BPL170630 | HYPH3170913 | H3FMA170713 |
| Hemagglutinin concentration (μgHA/mL) | 1493 | 1166 | 1954 |
| Protein content (μg/mL) | 2947 | 2269 | 5680 |
| Hemagglutinin content ratio (%) | 50.66 | 51.39 | 34.40 |

The invention claimed is:

1. A method for preparing an inactivated whole-virus influenza vaccine using an embryonated chicken egg technique, the method comprising:
    subjecting a virus solution, comprising whole influenza virus particles collected from embryonated chicken eggs, to a hypotonic treatment, which comprises contacting the virus solution with a hypotonic aqueous solution of 160 mOsm/kg or less to lower the osmolarity of the virus solution; and
    prior to or after subjecting the virus solution to a hypotonic treatment, inactivating the virus.

2. The method of claim 1, wherein the virus in the virus solution is inactivated prior to the hypotonic treatment.

3. The method of claim 1, wherein the hypotonic solution is an aqueous solution of 110 mOsm/kg or less.

4. The method of claim 1, wherein the virus in the virus solution is inactivated after the hypotonic treatment.

* * * * *